US008822171B1

(12) United States Patent
Anderton et al.

(10) Patent No.: US 8,822,171 B1
(45) Date of Patent: Sep. 2, 2014

(54) METHODS FOR SCREENING FOR INHIBITORS OF TAU PHOSPHORYLATION BY CASEIN KINASE I

(76) Inventors: Brian Anderton, London (GB); Diane Hanger, London (GB); Malcolm Ward, Cobham (GB); Helen Byers, Cobham (GB)

( * ) Notice: Subject to any disclaimer, the term of this patent is extended or adjusted under 35 U.S.C. 154(b) by 638 days.

(21) Appl. No.: 10/562,951

(22) PCT Filed: Jun. 25, 2004

(86) PCT No.: PCT/GB2004/002739
§ 371 (c)(1),
(2), (4) Date: Apr. 20, 2006

(87) PCT Pub. No.: WO2005/001114
PCT Pub. Date: Jan. 6, 2005

(30) Foreign Application Priority Data

Jun. 25, 2003 (GB) .................................. 0314943.2

(51) Int. Cl.
*C12Q 1/48* (2006.01)
(52) U.S. Cl.
USPC .......................................................... 435/15
(58) Field of Classification Search
None
See application file for complete search history.

(56) References Cited

U.S. PATENT DOCUMENTS

| 5,994,084 | A | * | 11/1999 | Anderton et al. .............. 435/7.1 |
| 6,057,117 | A | | 5/2000 | Harrison et al. |
| 6,593,512 | B1 | * | 7/2003 | Vitek et al. ...................... 800/18 |
| 2002/0172990 | A1 | * | 11/2002 | Curran et al. ................ 435/7.92 |

FOREIGN PATENT DOCUMENTS

WO     WO 95/19178     7/1995

OTHER PUBLICATIONS

Singh et al., "Comparison of the phosphorylation of microtubule-associated prote!n tau by non-proline dependent protein kinases", Molecular and Cellular Biochemistry 131:181-189, 1994.*
Chijiwa et al., J. Biol. Chem. 264:4924-4927, 1989.*
Lau et al., Current Topics in Medicinal Chemistry 2:395-415; 2002.*
Graves et al., J. Biol. Chem. 268:6394-6401; 1993.*
Zhu et al., Current Opinion in Chemical Biology 5:40-45, 2001.*
Hanger et al., J. Biol. Chem. 282:23645-23654, 2007.*
Hasegawa et al., J. Biol. Chem. 267:17047-17054, 1992.*
Morishima-Kawashima et al., J. Biol. Chem. 270:823-829, 1995.*
Ford et al., Prot. Exp. Purif. 2:95-107, 1991.*
Singh et al., Mol. Cell. Biochem. 131:181-189, 1994.*
Litersky et al., Biochem. J. 316:655-660, 1996.*
Yamamoto et al., Arch. Biochem. Biophys. 408:255-262, 2002.*

Singh et al., "Calcium/calmodulin-dependent protein kinase II phosphorylates tau at Ser-262 but only partially inhibits its binding to microtubules", FEBS Lett. 387:145-148, 1996.*
Meijer, L. et al., "Inhibition of cyclin-dependent kinases, GSK-3beta and CK1 by hymenialdisine, a marine sponge constituent," Chemistry and Biology, 7:51-63, (2000).
Kuret, J. et al., "Casein Kinase 1 is Tightly Associated with Paired-Helical Filaments Isolated from Alzheimer's Disease Brain," J. of Neurochemistry, 69:2506-2515, (1997).
Singh, T. et al., "Phosphorylation of tau Protein by Casein Kinase-1 Converts it to an Abnormal Alzheimer-Like State," J. of Neurochemistry, 64:1420-1423, (1995).
Lee G., et al., "Tyrosine Phosphorylation of Tau," Society for Neuroscience Abstracts, 27:1436, (2001).
Trojanowski, J., "Phosphorylation of paired helical filament tau in Alzheimer's disease neurofibrillary lesions: focusing on phosphatases," Faseb J., 9:1570-1576, (1995).
Larner, A., "Tau protein as a therapeutic target in Alzheimer's disease and other neurodegenerative disorders," Expert Opinion on Therapeutic Patents, 9:1359-1370, (1999).
Castro, A., et al., "Inhibition of tau phosphorylation: a new therapeutic strategy for the treatment of . . . ," Expert Opinion on Therapeutic Patents, 10:1519-1527, (2000).
Singh, T., et al., "Non-proline-dependent protein kinases phosphorylate several sites found in tau from Alzheimer . . . ," Molecular and Cellular Biochemistry, 154:143-151, (1996).
Roder, H., "Prospect of Therapeutic Approaches to Tauopathies," J. of Molecular Neuroscience, 20:197-201, (2003).
Ghoshal, N. et al., "A New Molecular Link between the Fibrillar and Granulovacuolar Lesions of Alzheimer's Disease," American Journal of Pathology, 155(4):1163-1172, (1999).
Hanger, D. et al., "New Phosphorylation Sites Identified in Hyperphosphorylated Tau (Paired Helical Filament-Tau) from . . . ," Journal of Neurochemistry, 71:2465-2476, (1998).
Lambert, M. et al., "Diffusible, nonfibrillar ligands derived from AB1-42 are potent central nervous system neurotoxins," Proc. Natl. Acad. Sci., 95:6448-6453, (1998).
Lee, V. et al., "Neurodegenerative Tauopathies," Annu. Rev. Neurosci., 24:1121-1159, (2001).
Mulot, S. et al., "PHF-tau from ALIzheimer's brain comprises four species on SDS-PAGE which can be . . . ," Federation of European Biochemical Societies, 349:359-364, (1994).
Shirazi, S. et al., "The protein tyrosine kinase, fyn, in Alzheimer's disease pathology," Neuro Report, 4:435-437, (1993).

(Continued)

*Primary Examiner* — David J Steadman
(74) *Attorney, Agent, or Firm* — Dann, Dorfman, Herrell & Skillman; Kathleen D. Rigaut; Robert C. Netter, Jr.

(57) ABSTRACT

Methods for screening for substances capable of modulating the phosphorylation of tau protein are disclosed, and in particular paired helical filament (PHF) tau, and the use of such modulators in the treatment of tauopathies. The assays and screening methods are based on the identification of new phosphorylation sites in PHF tau and new kinases and combinations of kinases as therapeutic targets, in particular the identification of casein kinase 1 as a kinase which phosphorylates tau protein.

11 Claims, No Drawings

(56) References Cited

OTHER PUBLICATIONS

Singh, T. et al., "Modulation of GSK-3-catalyzed phosphorylation of microtubule-associated protein tau by . . . ," Federation of European Biochemical Societies, 358:4-8, (1995).

Singh, T. et al., "Rapid Alzheimer-like phosphorylation of tau by the synergistic actions . . . ," Federation of European Biochemical Societies, 358:267-272, (1995).

Williamson, R. et al., "Rapid Tyrosine Phosphorylation of Neuronal Proteins Including Tau and Focal Adhesion Kinase in . . . ," The Journal of Neuroscience, 22(1):10-20 (2002).

Goedert, M. et al., "Cloning and sequencing of the cDNA encoding an isoform of microtubule-associated protein tau containing four . . . ," The EMBO Journal, 8(2):393-399 (1989).

Goedert, M. et al., "Expression of separate isoforms of human tau protein: correlation with the tau pattern in brain and . . . ," The EMBO Journal, 9(13):4225-4230, (1990).

Graves, P. et al., "Molecular Cloning, Expression, and Characterization of a 49-Kilodalton Casein . . . ," The Journal of Biological Chemistry, 268(9):6394-6401, (1993).

Goedert, M. et al., "Multiple Isoforms of Human Microtubule-Associated Protein Tau: Sequences and Localization in Neurofibrillary Tangles of . . . ," Neuron., 3:519-526, (1989).

Scales, T. et al., "Tyrosine Phosphorylation of Specific Sites on Tau by SRC Family Kinases," Neurobiol. Aging, 23:S500-S501, (2002).

N. Mashhoon et al., "Crystal Structure of a Conformation-Selective Casein Kinase-1 Inhibitor*", J. Biol. Chem., (2000).

* cited by examiner

METHODS FOR SCREENING FOR INHIBITORS OF TAU PHOSPHORYLATION BY CASEIN KINASE I

FIELD OF THE INVENTION

The present invention relates to methods for screening for substances capable of modulating the phosphorylation of tau protein, and in particular paired helical filament (PHF) tau, and the use of such modulators in the treatment of tauopathies. The assays and screening methods are based on the identification of new phosphorylation sites in PHF tau and new kinases and combinations of kinases as therapeutic targets.

BACKGROUND OF THE INVENTION

Alzheimer's disease (AD) is a neurodegenerative disease characterised by the presence of senile plaques and neurofibrillary tangles in the brain. The degree of dementia at death correlates better with neurofibrillary tangle numbers than with senile plaques counts. The presence of neurofibrillary tangles in neurons results in the death of those neurons, implying that prevention of tangle formation is an important therapeutic goal. The principal protein that forms the neurofibrillary tangle is the microtubule-associated protein, tau, which assembles into filaments that have the appearance of twisting about each other in pairs and are referred to as paired helical filaments (PHF). PHF are present in different locations in degenerating neurons in the Alzheimer brain and when many aggregate in the neuronal cell body, they produce the neurofibrillary tangle (Lee et al, 2001).

Senile plaques have an extracellular central deposit of amyloid β-peptide (Aβ), which is surrounded by dystrophic neurites to form the senile or neuritic plaque. In vitro and in vivo Aβ has been shown to be neurotoxic. Aβ is derived by proteolytic processing of the larger amyloid precursor protein (APP). Much attention has been focused on Aβ production as a therapeutic target because its production is believed to be an early event in AD pathogenesis. This is because mutations in the APP gene, which give rise to autosomal dominant AD, result in either increased overall production of Aβ or in a relative increase in the slightly longer $A\beta_{42}$ over $A\beta_{40}$, the former being more amyloidogenic; $A\beta_{42}$ has two additional hydrophobic amino acids at the C-terminus of 40-residue $A\beta_{40}$ thereby endowing the peptide with an increased tendency to aggregate and form amyloid fibres. Mutations in two other genes that also cause autosomal dominant AD, presenilin-1 and presenilin-2 (PS1 & PS2) also result in an increase in the ratio of $A\beta_{42}$ to $A\beta_{40}$. The belief that Aβ deposition in the brain precedes the appearance of neurofibrillary tangles has been the basis of the amyloid cascade hypothesis but it has been uncertain whether tangles are important in pathogenesis or are only an unimportant epiphenomenon. This has been changed by the discovery of mutations in the gene for tau in some other related neurodegenerative diseases.

The mechanism by which Aβ kills neurons in the brain has still to be established. Many studies of Aβ toxicity have been conducted in tissue culture using rat brain neuronal cultures. We have shown that exposure of both foetal rat and human brain neuronal cultures to aggregated Aβ induces within 2 to 10 minutes increases in the phosphotyrosine content of several proteins but also including tau (Williamson et al 2002). We have also shown that this treatment results in activation of the tyrosine kinase fyn, a member of the src family of tyrosine kinases. This tyrosine phosphorylation of tau was prevented by inhibitors of the src family of tyrosine kinases.

It has previously been reported that increased levels of fyn are associated with neurons containing abnormally phosphorylated tau in AD brain (Shirazi et al, 1993) and we have demonstrated using antibodies that recognise phosphotyrosine that PHF-tau from AD brain contains phosphotyrosine (Williamson et al 2002). We have shown in vitro that fyn and Lck, both src family kinases, phosphorylate recombinant human tau and phosphotyrosines 18, 310 and 394 were positively identified in one or more of their respective tryptic peptides, from sequence information of fragmented peptides. In addition, phosphotyrosine at position 197 was inferred from peptide masses in the survey scan (Scales et al, 2002).

Intraneuronal deposits of tau in the form of typical neurofibrillary tangles of AD or other morphologically distinct tau aggregates in a number of other neurodegenerative diseases, is the basis for grouping these conditions as tauopathies. Thus, in addition to AD, the main examples of the tauopathies are frontotemporal dementia with Parkinsonism linked to chromosome 17 (FTDP-17), progressive supranuclear palsy (PSP), Pick's disease, corticobasal degeneration, and multisystem atrophy (MSA). The intracellular tau deposits (usually neuronal but can also be glial) are all filamentous and mostly in a hyperphosphorylated state compared to the level of phosphorylation of tau from control human brain. In the case of AD, this hyperphosphorylated tau is often referred to as PHF-tau because it is derived from the PHF.

Other than for AD, deposits of Aβ in the brain are either absent or minimal in these other tauopathies. There are some tauopathy pedigrees with autosomal dominant disease in which the causative gene has been identified as the tau gene and although cases with the same mutation may present with apparently different diseases, they invariably have tau deposits in the brain and are mostly of the FTDP-17 variety. Thus, the finding of mutations in the tau gene which result in disease and deposition of tau aggregates in neurons is compelling evidence for the primary pathogenic importance of tau deposition in all of these conditions, including AD, whatever the primary cause of disease. Therefore, the amyloid cascade hypothesis is borne out by the discovery of tau mutations and confirms that indeed neurofibrillary tangle formation is almost certainly subservient to Aβ deposition in AD, but that in the other tauopathies lacking Aβ deposits, then some other primary event must trigger the tau pathology. Tau abnormalities and deposition are therefore important therapeutic targets for all tauopathies, including AD.

Tau is a phosphoprotein, the function of phosphorylation remaining to be unequivocally established. However, increased phosphorylation of tau on multiple serine and threonine residues reduces the ability of tau to promote microtubule assembly and to stabilise assembled microtubules, effects that have been demonstrated both in vitro and in cells. Many studies have shown that PHF-tau from AD brain is more heavily phosphorylated on serine and threonine than tau from control brain. This has been demonstrated partly by protein sequencing and partly by demonstrating that certain monoclonal antibodies only label either PHF-tau or non-phosphorylated tau and not PHF-tau; the epitopes for many of these antibodies have been mapped to particular phosphorylated residues present in PHF-tau and absent from control brain tau. The pathological tau from most other cases of other tauopathies seems to be similarly hyperphosphorylated to PHF-tau.

These findings strongly imply that similar abnormalities in regulating phosphorylation of tau are shared by all the tauopathies including AD. Since phosphorylation of proteins is effected by protein kinases and dephosphorylation by protein phosphatases, identifying the protein kinases and phosphatases for tau is important because they are potentially therapeutic targets for these diseases.

It remains a considerable problem in the art in identifying the enzymes responsible for causing phosphorylation of paired helical filament tau and the sites phosphorylated by those enzymes.

SUMMARY OF THE INVENTION

Broadly, the present invention relates to the modulation of the phosphorylation of tau protein through its interaction with kinases and phosphatases. In particular, it is based on the identification of new sites in tau protein that are susceptible to phosphorylation by kinases and to the identification of kinases and combinations of kinases that are capable of phosphorylating new and known phosphorylation sites in tau protein. Importantly, many of the newly identified sites are present in paired helical filament (PHF) tau, and not in control tau or fetal tau.

The present invention is based on the analysis by mass spectrometry PHF-tau and tau from control adult and foetal rat brain, and identifies 12 new sites in PHF-tau, bringing the total to 37 phosphorylation sites (1 site is tyrosine 394 and the other 36 are either serine or threonine residues) and this with >90% sequence coverage. Of these 12 sites, 11 have not been found in tau from normal human brain.

A number of protein kinases have been demonstrated to phosphorylate tau in vitro, including glycogen synthase kinase-3α (GSK-3α), glycogen synthase kinase-3β (GSK-3β), MAP kinases (ERKs 1 & 2), cdk5, cdc2 kinase, JNK, several members of the SAP kinases (1γ, 2a, 2b, 3, 4), p38MAP kinase, calmodulin-dependent kinase, protein kinase A (PKA), protein kinase C (PKC), casein kinase 1 (CK1), casein kinase 2 (CK2), MARK, PKN, PKB, TTK, DYRK, Rho kinase and phosphorylase kinase. Of these kinases, GSK-3 has been demonstrated to phosphorylate the greatest number of identified sites in PHF-tau, this being 25 sites, including 2 sites that are generated by GSK-3 only when tau is already phosphorylated and PKA phosphorylates 16 sites in PHF-tau. We have now shown also by in vitro phosphorylation that CK1 is also a candidate kinase for 6 of the 12 newly identified sites, GSK-3 phosphorylates 4 of these and PKA phosphorylates 2 of the new PHF-tau sites. This brings the total number of sites in PHF-tau that can be phosphorylated by CK1 to 17 sites.

The MAP kinases (ERKs 1 & 2), cdk5, cdc2 kinase, JNK, several members of the SAP kinases (1γ, 2a, 2b, 3, 4), and p38MAP kinase are similar in specificity to GSK-3, being essentially proline-directed protein kinases and they all phosphorylate most of the sites phosphorylated by GSK-3. Thus, after these proline-directed protein kinases, CK1 is now the most conspicuous kinase as a candidate for contributing to generating the phosphorylation state of PHF-tau, with only 18 CK1 sites definitely shared by GSK-3. Therefore, of the 36 ser/thr sites in PHF-tau, 31 could potentially be phosphorylated by a combination of GSK-3, CK1, and PKA, and the additional 5 sites remain as orphan sites with no kinase known to phosphorylate these residues. It is possible that GSK-3, CK1 or PKA could phosphorylate some or all of these orphan sites or indeed that one or more of the other potential tau kinases listed above could be responsible and the phosphorylated sites have not been detected. However, the data disclosed herein imply that CK1 should be considered as a strong candidate for generating hyperphosphorylated tau in AD and the other tauopathies and hence is a potential therapeutic target.

Of the known phosphorylation sites in PHF-tau, several are considered to be particularly important. Monoclonal antibody, AT100, of all such antibodies is the most specific for PHF-tau since it does not recognise normal brain tau nor foetal tau; as such it is considered to be diagnostic for pathological hyperphosphorylated tau in the tauopathies. The AT100 epitope requires phosphorylation of both T212 and S214. It is known that T212 and S214 can be phosphorylated by GSK-3 and it has been reported that phosphorylation T212 by GSK-3 primes tau for phosphorylation at S214 by PKA (Singh et al, 1995a,b). We have found that CK1 is also able to phosphorylate S214, thereby further implicating CK1 in pathological phosphorylation.

One other site in tau, S262, has been shown to be important in regulating the binding of tau to microtubules such that phosphorylation causes dissociation of tau. A novel kinase, MARK, that phosphorylates tau at this site was isolated from brain and proposed as the responsible kinase. We have found that CK1 is also able to phosphorylate S262 and S356, the latter being an homologous residue that may behave like S262 in contributing to regulating binding of tau to microtubules and we have found that both S262 and S356 are phosphorylated in PHF-tau.

Thus, the above two classes of phosphorylation of tau that are considered to be important could be regulated by CK1. Furthermore, it has been reported that CK1, particularly the CK1δ isoform, is elevated in brain extracts from AD cases compared to controls, which adds to the potential importance of CK1 in pathogenesis (Ghoshal et al, 1999).

With respect to tyrosine phosphorylation, PHF-tau is phosphorylated on tyrosine 394 and fyn is the strongest candidate although other src family kinases may also phosphorylate tau in brain.

Accordingly, in one aspect, the present invention proposes that CK1 is a novel therapeutic target for treating AD and other related tauopathies.

In a further aspect, the present invention proposes that fyn and related src family kinases are novel therapeutic targets for treating AD and other related tauopathies, in particular for tyrosine phosphorylation sites disclosed herein.

In a further aspect, the present, invention proposes new phosphorylation sites in tau protein for use in screening for inhibitors of phosphorylation or promoters of dephosphorylation, optionally used in combination with the kinases identified herein as being capable of phosphorylating the sites.

As a consequence of these findings, the new sites and kinases can be used as the basis of assays and assay methods for screening for modulators of the phosphorylation of the sites in tau protein for use or development as therapeutics for the treatment of tauopathies. Preferred modulators are capable of inhibiting the phosphorylation of tau to produce a phosphorylated state similar or identical to that of PHF-tau and/or promoting the dephosphorylation of phosphorylated forms of PHF-tau.

Eleven of the new phosphorylation sites in tau protein are shown in Table 2 in red type in the left hand column. They are the serine and threonine residues at positions S68, T69, T71, (T111/S113), S191, S258, S289, (T414/S416), T427, S433 and S435. A further tyrosine site at position 394 (Y394) has also been identified (e.g. phosphorylated by tyrosine kinases and dephosphorylated by tyrosine phosphatases). Of the 12 sites, 10 are only found in PHF-tau, see Table 2 comparing the PHF tau and control tau columns.

Accordingly, in a further aspect, the present invention provides the use of a tau protein comprising one or more of these phosphorylation sites as defined herein for screening for candidate substances which are capable of inhibiting phosphorylation at the site(s) by a kinase or promoting dephosphorylation of a phosphorylated site by a phosphatase.

In the present invention, the taut protein comprising the phosphorylation sites may be substantially full length and/or wild type tau or PHF-tau protein, or may be a fragment, active portion or sequence variant thereof. In other embodiments, the present invention may employ a corresponding nucleic acid molecule encoding the tau protein. Where a tau protein which is a fragment, active portion or sequence variant is employed, the phosphorylation site(s) may be present with surrounding amino acids from the tau protein sequence. Preferably, the present invention employs PHF-tau protein. In the present invention the numbering of tau and PHF-tau is according to the sequence of the longest brain isoform of human tau (441 amino acids) disclosed in Goedert et al (1989) EMBO J. 1989 February; 8(2):393-9. Cloning and sequencing of the cDNA encoding an isoform of microtubule-associated protein tau containing four tandem repeats: differential expression of tau protein mRNAs in human brain. Goedert M, Spillantini M G, Potier M C, Ulrich J, Crowther R A; or Goedert M, Jakes R. (1990) Expression of separate isoforms of human tau protein: correlation with the tau pattern in brain and effects on tubulin polymerization. EMBO J., 9, 4225-30.

Alternatively or additionally, any of the above defined tau proteins may possess phosphorylation at one or more of the phosphorylation sites. This enables the effects of cooperative phosphorylation of the protein to be studied, that is, where the phosphorylation of one site is dependent in changes to the tau protein caused by one or more preceding or simultaneous phosphorylation steps. Thus, in some embodiments of the present invention, the tau protein may include one or more of the known tau phosphorylation sites, for example those set out in Table 2, left hand column in black type, in addition to one or more of the newly found sites, and optionally have phosphorylation at one or more of those additional sites.

In a further aspect, the present invention provides a method of screening for substances which are capable of inhibiting phosphorylation at one or more of the site(s) of a tau protein by a kinase, wherein the tau protein comprises one or more phosphorylation sites disclosed herein, the method comprising:
(a) contacting at least one candidate substance, the tau protein as defined herein and a kinase which is capable of phosphorylating the tau protein under conditions in which the kinase is capable of phosphorylating the site(s) of the tau protein in the absence of the candidate substance;
(b) determining whether, and optionally the extent to which, the candidate substance inhibits the phosphorylation of the tau protein at one or more sites of the tau protein; and,
(c) selecting the candidate substance which inhibits phosphorylation of the tau protein at one or more of the sites.

In a further aspect, the present invention provides a method of screening for substances which are capable of promoting dephosphorylation at one or more of the site(s) of a tau protein by a phosphatase, wherein the tau protein comprises one or more sites as defined herein, the method comprising:
(a) contacting at least one candidate substance, the tau protein as defined herein and a phosphatase which is capable of dephosphorylating the tau protein under conditions in which the phosphatase is capable of dephosphorylating the site(s) of the tau protein in the absence of the candidate substance;
(b) determining whether, and optionally the extent to which, the candidate substance promotes the dephosphorylation of the tau protein at one or more sites of the tau protein; and,
(c) selecting the candidate substance which promotes dephosphorylation of the tau protein at one or more of the sites.

In some embodiments, the method may comprise, having identified a candidate substance according to one of the methods disclosed herein, the further step(s) of optimising the candidate substance to improve one or more of its properties and/or formulating it as a pharmaceutical.

In the methods and uses disclosed herein, preferably the kinase is selected from casein kinase 1 (CK1), casein kinase 2 (CK2), protein kinase A (PKA), glycogen synthase kinase 3α (GSK-3α), and glycogen synthase kinase 3β (GSK-3β). More preferably, the kinase is CK1 or a combination (either simultaneously or sequentially applied) of CK1, PKA and GSK-3β.

In the present invention, preferably the step of detecting the presence and extent of phosphorylation and dephosphorylation in the tau protein can be carried out using mass spectroscopy as described in detail below. Alternatively, or additionally, site specific recognition agents which are capable of distinguishing between a site which is phosphorylated and one which is not may be used. Examples of such agents known in the art are site specific antibodies such as monoclonal antibody AT100.

In a further aspect, the present invention provides a substance obtainable from one of the methods disclosed herein which is capable of inhibiting the phosphorylation or promoting the dephosphorylation of a tau protein at one or more of the above defined sites.

A further aspect of the present invention is based on the finding that casein kinase 1 is capable of phosphorylating a tau protein at previously unknown positions. Some of the positions are known or suspected in the art of being phosphorylation sites, while others are among the phosphorylation sites identified herein for the first time. The sites of PHF-tau protein that are phosphorylated by CK1 include (S46/T50), S113, S131, T149, T169, S184, S208, (S210/T212), S214, S237, S238, S241, S258, S262, T263, S285, S289, S305, S341, S352, S356, T361, T373, T386, (S412/S413/T414/S416-two of these four), S416, S433 and S435. Of these sites, S113, 184, 208, (210/212), 214, 237, 238, S258, S289, S433 and S435 are disclosed as phosphorylation sites of PHF-tau protein for the first time herein. The sequence of casein kinase 1 is provided in J Biol. Chem. 1993 Mar. 25; 268(9):6394-401. Molecular cloning, expression, and characterization of a 49-kilodalton casein kinase I isoform from rat testis. Graves P R, Haas D W, Hagedorn C H, DePaoli-Roach A A, Roach P J.

Accordingly, the present invention provides the use of a casein kinase 1 as defined herein (including fragments, active portions or sequence variants), or a corresponding nucleic acid molecule, for screening for candidate compounds which are capable of (a) inhibiting the activity of casein kinase 1 in phosphorylating a tau protein such as paired helical filament tau or (b) binding to casein kinase 1 to inhibit its interaction with a tau protein such as paired helical filament tau.

In a further aspect, the present invention provides a method of screening for substances which are capable of inhibiting the phosphorylation of a tau protein by casein kinase 1 (CK1), wherein the tau protein comprises one or more phosphorylation sites disclosed herein, the method comprising:
(a) contacting at least one candidate substance, the tau protein as defined herein and casein kinase 1 under conditions in which the casein kinase 1 is capable of phosphorylating the site(s) of the tau protein in the absence of the candidate substance;
(b) determining whether, and optionally the extent to which, the candidate substance inhibits the phosphorylation of the tau protein at one or more sites of the tau protein by casein kinase 1; and,
(c) selecting the candidate substance which inhibits phosphorylation of the tau protein at one or more of the sites.

In a further aspect, the present application also discloses that a combination of kinases is required to phosphorylate the majority of the phosphorylation sites disclosed herein or in the prior art. In the experiments disclosed herein, a combination of casein kinase 1 (CK1), protein kinase A (PKA) and glycogen synthase kinase 3β (GSK-3β) was found to be capable, either alone or in cooperation, of phosphorylating the majority of the phosphorylation sites of tau protein and in particular PHF-tau protein. This combination of kinases can be used simultaneously or sequentially to screen for modulators of tau phosphorylation, in contrast to prior art proposals that have focussed on screening using a single kinase.

Accordingly, the present invention provides the use of a casein kinase 1 (CK1), protein kinase A (PKA) and glycogen synthase kinase 3β (GSK-3β) (including fragments, active portions or sequence variants), or a corresponding nucleic acid molecule, for screening for candidate compounds which are capable of (a) inhibiting the activity of casein kinase 1 in phosphorylating a tau protein or (b) binding to casein kinase 1 to inhibit its interaction with a tau.

In a further aspect, the present invention provides a method of screening for substances which are capable of inhibiting the phosphorylation of a tau protein by casein kinase 1 (CK1), protein kinase A (PKA) and glycogen synthase kinase 3β (GSK-3β), wherein the tau protein comprises one or more phosphorylation sites disclosed herein, the method comprising:
(a) contacting at least one candidate substance, the tau protein as defined herein and casein kinase 1 (CK1), protein kinase A (PKA) and glycogen synthase kinase 3β (GSK-3β) under conditions in which the kinases are capable of phosphorylating the site(s) of the tau protein in the absence of the candidate substance;
(b) determining whether, and optionally the extent to which, the candidate substance inhibits the phosphorylation of the tau protein at one or more sites of the tau protein by the kinases; and,
(c) selecting the candidate substance which inhibits phosphorylation of the tau protein at one or more of the sites.

In this aspect of the invention, one or more of these kinases may be substituted by a kinase having the same or a similar activity and/or substrate specificity.

Embodiments of the present invention will now be discussed in more detail by way of example and not limitation with reference to the accompanying tables.

TABLES

Table 1 summarises the new sites found in the work leading to the present invention and the kinases capable of acting at those sites. Tables 2 and 3 present this data in more detail.

SEQ ID NO: 1 shows the amino acid sequence of rat casein kinase 1, a 428 amino acid protein.

SEQ ID NO: 2 shows the amino acid sequence of the long form of human tau protein, a 441 amino acid protein.

SEQ ID NO: 3 shows the amino acid sequence of human fyn kinase, a 537 amino acid protein.

DETAILED DESCRIPTION

Tau Proteins

The assays and assay methods disclosed herein can employ wild-type or full length tau proteins, kinases or phosphatases or fragments, active portions or derivatives thereof. In the case of tau proteins, the materials used in the assays may be unphosphorylated or partially phosphorylated as discussed above.

In the present invention, derivatives of the tau proteins, kinases (especially CK1 kinase or fyn kinase) or phosphatases have an amino acid sequence which differs by one or more amino acid residues from the wild-type amino acid sequence, by one or more of addition, insertion, deletion and substitution of one or more amino acids. Thus, variants, derivatives, alleles, mutants and homologues, e.g. from other organisms, are included. Thus, a derivative of tau protein or CK1 kinase or fyn kinase may include 1, 2, 3, 4, 5, greater than 5, or greater than 10 amino acid alterations such as substitutions with respect to the wild-type sequence.

Preferably, a fragment or derivative of a protein used in the assays disclosed herein preferably shares sequence identity with the corresponding portion of the relevant wild-type sequence of the protein, and preferably has at least about 60%, or 70%, or 75%, or 80%, or 85%, 90% or 95% sequence identity. As is well-understood, identity at the amino acid level is generally in terms of amino acid identity which may be defined and determined by the TBLASTN program, of Altschul et al. (1990) J. Mol. Biol. 215: 403-10, which is in standard use in the art. Identity may be over the full-length of the relevant peptide or over a contiguous sequence of about 5, 10, 15, 20, 25, 30, 35, 50, 75, 100 or more amino acids, compared with the relevant wild-type amino acid sequence. Alternatively, nucleic acid encoding a fragment or derivative may hybridise to the corresponding wild type nucleic acid under stringent conditions, for example as disclosed in textbooks such as Ausubel, Short Protocols in Molecular Biology, 1992 or Sambrook et al, Molecular Cloning, A Laboratory Manual, Cold Spring Harbor Laboratory Press, 1989, using a hybridization solution comprising: 5×SSC, 5×Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5°\ C. + 16.6\ \text{Log}\ [Na+] + 0.41\ (\%\ G+C) - 0.63\ (\%\ \text{formamide}) - 600/\#bp\ \text{in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Methods of Screening for Inhibitors and Enhancers

It is well known that pharmaceutical research leading to the identification of a new drug may involve the screening of very large numbers of candidate substances, both before and even after a lead compound has been found. This is one factor which makes pharmaceutical research very expensive and time-consuming. Means for assisting in the screening process can have considerable commercial importance and utility.

As detailed above, methods of screening for a substance which are inhibitors of phosphorylation of tau protein or promoters of dephosphorylation of tau protein can be carried out by contacting one or more test substances with the tau protein and kinase or phosphatase (as defined herein) in a suitable reaction medium, and determining the presence or extent of phosphorylation of dephosphorylation in the presence and absence of the candidate substance. A difference in activity in the presence and absence of the candidate substance is indicative of a modulating effect.

Preliminary assays in vitro may be followed by, or run in parallel with, in vivo assays.

Of course, the person skilled in the art will design any appropriate control experiments with which to compare results obtained in test assays.

Performance of an assay method according to the present invention may be followed by isolation and/or manufacture and/or use of a compound, substance or molecule which tests positive for ability to modulate interaction between one of the phosphorylation sites of tau protein (as defined herein) and a kinase (such as CK1 or a combination of CK1, PKA and GSK-3β) or a phosphatase.

The precise format of an assay of the invention may be varied by those of skill in the art using routine skill and knowledge. For example, interaction between substances may be studied in vitro by labelling one with a detectable label and bringing it into contact with the other which has been immobilised on a solid support. Suitable detectable labels, especially for peptidyl substances include $^{35}$S-methionine which may be incorporated into recombinantly produced peptides and polypeptides. Recombinantly produced peptides and polypeptides may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

The amount of a candidate substance which may be added to an assay of the invention will normally be determined by trial and error depending upon the type of compound used. Typically, from about 0.001 nM to 1 mM or more concentrations of putative inhibitor compound may be used, for example from 0.01 nM to 100 µM, e.g. 0.1 to 50 µM, such as about 10 µM. Greater concentrations may be used when a peptide is the test substance. Even a molecule which has a weak effect may be a useful lead compound for further investigation and development.

Combinatorial library technology provides an efficient way of testing a potentially vast number of different substances for ability to modulate activity of a polypeptide. Such libraries and their use are known in the art. Compounds which may be used may be natural or synthetic chemical compounds used in drug screening programmes. Extracts of plants which contain several characterised or uncharacterised components may also be used.

Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction. Antibodies may also be employed as site specific recognition agents for determining whether phosphorylation of a site in tau protein has occurred during an assay.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO 92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. Cloning and expression of chimeric antibodies are described in EP 0 120 694 A and EP 0 125 023 A.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. The mode of determining binding is not a feature of the present invention and those skilled in the art are able to choose a suitable mode according to their preference and general knowledge.

Mass Spectroscopy

An LC/MS/MS based strategy was used to discover new phosphorylation sites within tau protein isolated from AD brain. So called PHF-tau was initially extracted from a heat-stable preparation of human AD brain material and subsequently further purified by ion exchange chromatography. Having been separated using SDS-PAGE, phospho-peptide mapping was then undertaken. Coomassie stained bands are excised, reduced, alkylated and enzymatically digested using a suite of proteases such as trypsin, chymotrypsin and endoproteinase Asp-N. Resulting peptide mixtures are then analysed by LC/MS/MS using a Q-TOF micro instrument with peptide separation achieved using a 75 micron ID Pep-Map reversed phase column with peptides eluted using a gradient of acetonitrile at a flowrate of 200 nl/min.

Database searching against bespoke index files is performed utilising the Mascot algorithm (Matrix Science). All MS/MS spectra relating to phosphopeptides are then subsequently visually verified to check the result.

Tandem MS/MS of peptides may be used to provide sequence information by virtue of the fragment ions produced. Fragmentation occurs generally across the peptide bond leading to a ladder of sequence ions that are diagnostic of the amino acid sequence. The difference between consecutive ions in a series indicates the mass of the amino acid at that position in the peptide. The most common ion types are b and y ions. The C-terminal containing fragments are designated y-ions and the N-terminal containing fragments are designated b-ions (Roepstorff, P., Fohlman, J. J. Biomed. Mass Spectrom. 1984, 11, 601). Peptides created by trypsin proteolysis and ionised by electrospray generally form ions that are doubly charged. This stems from the presence of basic groups within the peptide, namely, the alpha amino group at the N-terminus and the side chain of the C-terminal lysine or arginine. MS/MS spectra of such peptides generally yield a prominent y-type ion series in the high mass end of the spectrum (Bonner, R., Shushan, B. Rapid Commun. Mass Spectrom. 1995, 9, 1067-1076). Ideally, for de novo sequencing purposes, a complete set of complementary b and y ions will ensure a high confidence level for the proposed peptide sequence. Moreover, if fragment ions representing the complete sequence of the peptide are present, the site of attachment of the phosphate group can be deduced from the position and pattern of these fragment ions. Therefore, it is possible in most instances to discover the exact site of phosphorylation in each phosphopeptide. In some instances we have even found MS/MS spectra to be heterogeneous. Here two (or more) distinct phosphopeptides are represented in the same spectrum. This is because each phosphopeptide form has the same molecule weight and the same number of phosphate groups, but these are attached to different amino acids within the peptide. Therefore, both forms give rise to precursor ions of the same m/z ratio, which are then selected simultaneously by the mass spectrometer during the MS/MS experiment. In such cases, we refer to the phosphopeptides concerned as "regiomers"

Multiplex Assays for Screening Compounds

In drug development it is desirable to develop rapid high throughput assays with simple read out to show whether a compound has an effect on the proposed target. In the case of compounds inhibiting an enzyme function., such as a kinase, it is possible to develop an artificial substrate for the target enzyme that is modified by the enzyme in a way that the level of modification can be readily detected. In the presence of an inhibitory compound, the substrate is not modified and this can also be readily detected.

In the case of inhibitors of tau phosphorylation, it is necessary to monitor the effect of inhibiting specific protein kinases on the phosphorylation status of a large number of sites. In one aspect, it is possible to prepare artificial substrates corresponding to each of the phosphorylation sites on tau and assess each compound for their ability to inhibit the phosphorylation of each site independent of the other sites. In such a system, each compound would be added to multiple wells each well containing the proposed kinase target, one of the phosphorylation site-specific artificial substrates and a reporter system to show phosphorylation, such as a monoclonal antibody that binds specifically to the substrate in either the phosphorylated or unphosphorylated form, and which antibody is labelled with a fluorescent marker, an enzyme that converts a colour less substrate into a coloured product, or an enzyme that promotes the production of a luminescent signal. In such an assay, it is desirable that the artificial substrate for the target is immobilised on a solid surface such that as part of the assay procedure any unreacted antibody is removed from the system by washing before the result is read. Such assays may be run in microtitre wells of varying formats of typically 96, or more typically 384, or even more typically 1536 wells, or alternatively may be run on a microarray based on a solid support such as glass.

Alternatively, the effect of different kinase inhibitors on the global phosphorylation status of tau may be designed. In such an assay, full length recombinant tau protein carrying no phosphorylations, or one or more desirable phosphorylations may be used as the substrate. Alternatively, a mixture of equal amounts of all of the artificial substrates representing single phosphorylation sites may be used. Each screening assay will determine the effect of compounds on the inhibition of one, two or more protein kinases with known activity for the phosphorylation of tau. As with the more simple assays described above substrate, target kinase and compound are added to a well of a microtitre plate and incubated with appropriate buffers and other constituents that permit the phosphorylation of substrate in the absence of an inhibitory compound. The phosphorylation status of the substrate may then be determined using a mixture of antibodies or other molecules with specificity for individual phosphorylation sites on tau, wherein such antibodies or other molecules are each labelled with a unique reporter such as a fluorescent dye or compounds with unique spectral properties in infra-red, visible or ultraviolet spectra. After removal of antibodies that remain unbound to the phosphorylated substrate(s), levels of each specific reporter are determined using an appropriate reading device, and the levels of phosphorylation at each specific site in tau is revealed by comparison with a control where no kinase inhibitor was added.

In a preferred embodiment of such a multiplex screening assay, the substrate is dephosphorylated recombinant tau protein and the kinase is selected from CK1, CK2, GSK-3a, GSK-3b, PKA, CDK5, ERK1/2, SAPK1g, SAPK2a, SAPK2b, SAPK3, SAPK4, stress activated protein kinase family kinases (SAPKs) such as p38MAPK and JNK, MARK family kinases such as 110K, cdc2, cdk2, PKC, PKN, TTK, PKB, DYRK, PK, CaMKII, PKD, Rho kinase, or a mixture of one of more these kinases. Reporter systems are preferably labelled antibodies, typically monoclonal antibodies, for example those that can be obtained from rabbits or mice using techniques well known in the art. Labels are preferably fluorescent or colorimetric compounds that are covalently attached to antibodies, more preferably fluorescent or colorimetric nanoparticles and are most preferably nanoparticles with unique Raman spectra.

Development of Mimetic Substances

Other candidate inhibitor compounds may be based on modelling the 3-dimensional structure of a polypeptide or peptide fragment and using rational drug design to provide potential inhibitor compounds with particular molecular shape, size and charge characteristics.

Once candidate substance have been found in the assays and screens according to the present invention, they may be used to design mimetic compounds for development as drugs. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Pharmaceutical Compositions

Following identification of a substance which modulates or affects phosphorylation or dephosphorylation of tau protein, the substance may be investigated further. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified using the screening assays and assay methods disclosed herein, but also a pharmaceutical composition, medicament, drug or other composition comprising such a substance, a method comprising administration of such a composition to a patient, e.g. to treat tauopathies, use of such a substance in manufacture of a composition for administration for the treatment of tauopathies, and a method of making a pharmaceutical composition comprising admixing such a substance with a pharmaceutically acceptable excipient, vehicle or carrier, and optionally other ingredients.

The substances identified as kinase inhibitors or phosphatase promoters in the assays and assay methods of the present invention, or compounds or substances arising from further development or optimisation, may be formulated in pharmaceutical compositions. These compositions may be employed for the treatment of tauopathies, that is conditions which are characterised by neurofibrillary tangles or aggregates of tau protein. Tauopathies are a recognised class of conditions known to those skilled in the art and include Alzheimer's disease, frontotemporal dementia with Parkinsonism linked to chromosome 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Sträussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonism-dementia complex, non-Guamanian motor neuron disease with neurofibrillary tangles/dementia, and Parkinson's disease. The intracellular tau deposits are usually neuronal or glial and are filamentous and generally in a hyperphosphorylated state as compared to the level of phosphorylation in tau from control human brain. In the case of AD, this hyperphosphorylated tau is often referred to a paired helical filament tau (PHF) tau because it is derived from the PHF.

These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site off delivery, the method of administration and other factors known to practitioners. Examples of the techniques and protocols mentioned above can be found in Remington's Pharmaceutical Sciences, 20th Edition, 2000, pub. Lippincott, Williams & Wilkins. A composition may be administered alone or in combination with other treatments, either simultaneously or sequentially, dependent upon the condition to be treated.

Materials and Methods
Mass Spectrometry
Data Acquisition

Following SDS-PAGE the gel bands relating to PHF-tau were excised, reduced, alkylated and digested with trypsin. Peptides were extracted from the gel pieces by a series of acetonitrile and aqueous washes. The extract was pooled with the initial supernatant and lyophilised. Each sample was then resuspended in 6 ml of 50 mM ammonium bicarbonate and analysed by LC/MS/MS. Chromatographic separations were performed using an Ultimate LC system (Dionex, UK). Peptides were resolved by reverse phase chromatography on a 75 mm C18 PepMap column. A gradient of acetonitrile in 0.05% formic acid was delivered to elute the peptides at a flow rate of 200 nl/min. Peptides were ionised by electrospray ionisation using a Z-spray source fitted to a Q-Tofmicro (Micromass, UK). The instrument was set to run in automated switching mode, selecting precursor ions based on their intensity, for sequencing by collision-induced fragmentation.

Data Analysis

The mass spectral data was processed into peak lists and searched against the full-length sequence of Tau-6 (441 amino acids; mw 45847) using Mascot software (Matrix Science, UK). Phosphorylated peptides were identified by selecting phosphate as a variable modification within the searching parameters. Serine, threonine and tyrosine phosphorylation were all considered. The exact location of the modification within each peptide was determined by the pattern of fragment ions produced (see below for further explanation).

Tandem Mass Spectrometry

To obtain definitive evidence and determine the exact site of phosphorylation, peptides were separated by reversed-phase chromatography and sequenced by tandem MS/MS. In these experiments precursor ions relating to each of the phosphopeptides are individually selected and subjected to collision induced dissociation (CID). Fragment ions so produced are indicative of the sequence of the phosphopeptide and the site of modification is determined by the molecular weight of the relevant fragment ions. Conversely, other potential sites of phosphorylation within particular phosphopeptides can also be ruled out by the presence of other fragment ions within the MS/MS spectrum.

An unexpected observation is that on some occasions it has been possible to pinpoint several discrete forms of phosphopeptides within a single MS/MS spectrum. Here the phosphopeptides each have the same molecular weight (and so are selected simultaneously), but differ in the site(s) of phosphorylation. Thus, the fragment ions observed are effectively a composite representation of each molecule being analysed.

Purification of PHF-Tau from Alzheimer Brain

Paired helical filament (PHF) tau was purified from Alzheimer brain as described in (Hanger et al, 1998). Briefly, brain tissue was homogenised and insoluble PHF-tau was recovered by differential centrifugation. Following solubilisation in guanidine and dialysis against a re-naturing buffer, PHF-tau was purified by anion-exchange and reversed-phase chromatography.

Preparation and Purification of Recombinant Human Tau

A plasmid expressing the largest tau isoform (2N4R) was used to prepare and purify recombinant human tau as described previously (Mulot et al, 1994). Briefly, a bacterial cell lysate expressing 2N4R tau was heated and centrifuged to remove heat-labile proteins. The supernatant was fractionated with ammonium sulphate and precipitated material was solubilised and dialysed into buffer prior to cation-exchange chromatography. Proteins were eluted with NaCl and fractions containing tau were pooled and dialysed against ammonium bicarbonate before lyophilisation.

In Vitro Phosphorylation of Recombinant Tau by Serine-/Threonine Protein Kinases Recombinant human tau (40 µg/ml) was incubated with 67 U/ml casein kinase 1 (CK1), 67 U/ml casein kinase 2 (CK2), 167 U/ml cyclic AMP-dependent protein kinase (PKA), 67 U/ml glycogen synthase-3β (GSK-3β) or all four kinases in combination, each at the stated concentration, in the presence of 3 mM ATP for 6 h at 30° C. Each kinase was obtained in a purified recombinant form from New England Biolabs.

In-Gel Proteolytic Digestion of Tau

PHF-tau or in vitro phosphorylated tau proteins were separated on 10% (wt/vol) polyacrylamide gels and stained with colloidal Coomassie Blue G. Protein bands corresponding to tau were excised, carbamidomethylated, and digested with proteolytic enzymes (trypsin or Asp-N). Peptides were extracted from gel pieces by a series of acetonitrile and aqueous washes, dried and resuspended in 50 mM ammonium bicarbonate.

Amyloid Beta Treatment of Neurons

Rat and human cortical neurons were treated with Aβ peptide (25-35) or reverse Aβ peptide (35-25) for 1-10 min.

Proteins containing phosphotyrosine were immunoprecipitated and separated by SDS-PAGE. Western blots of heat-stable extracts of neuronal cultures and immunoprecipitates were probed with antibodies to tau.

Results

New Sites Found in PHF-Tau

Current literature reports 25 known phosphorylation sites (all are serine or threonine) identified by direct means in PHF-tau (Hanger et al, 1998). There are a further 2-3 sites that have been identified by antibody reactivity only. We have found an additional 12 phosphorylation sites in PHF-tau, one of which is a tyrosine residue (tyr394), bringing the total number of sites to 37. Four of the new sites are more amino terminal in tau than any previously reported sites and three sites are more carboxy terminal than found previously. Of the 12 new sites, 4 are present in alternatively-spliced regions of tau and therefore are present only in specific taut isoforms, all previously identified PHF-tau phosphorylation sites are present in all tau isoforms. Only one of the 12 new sites in PHF-tau (either thr414 or ser416) is detected in tau from normal brain (ser416).

New Sites on Recombinant Tau for Each of the 4 Serine/Threonine Kinases Investigated See also Table 1

CK1 found 28 new sites making a total of 30 sites in all. 17 CK1 sites are present in PHF-tau, including 15 of the new CK1 sites. CK1 is a candidate kinase for 6 of the 12 new PHF-tau sites.

CK2 found 5 new sites making a total of 8 in all. 5 CK2 sites are present in PHF-tau, including 3 of the new CK2 sites. CK2 is a candidate kinase for 1 of the 12 new PHF-tau sites GSK-3 found 12 new sites making a total of 38 in all. 21 GSK-3 sites are present in PHF-tau, including 5 of the new GSK-3β sites. GSK-3 is a candidate kinase for 4 of the 12 new PHF-tau sites PKA found 5 new sites making a total of 24 in all. 16 PKA sites are present in PHF-tau, including 4 of the new PKA sites. PKA is a candidate kinase for 2 of the 12 new PHF-tau sites Comparing PHF-tau phosphorylation sites with the recombinant tau and kinase data, when all of the phosphorylation sites for CK1, GSK-3β, and PKA are combined, 30-33 of the 37 PHF-tau sites are phosphorylated (3 sites are defined only as one of two adjacent residues). Of the residual 4 to 7 sites, one is a tyrosine residue that requires tyrosine kinase activity, 4 other sites have no known kinase and the remaining 2 sites are each contained within regions where only 1 of 2 nearby residues are phosphorylated (T111 and S185).

Seven of the 12 new phosphorylation sites in PHF-tau could be generated by CK1, GSK-3, or PKA, four have no known kinase and the fifth site required a tyrosine kinase for phosphorylation.

Combining the four kinases together in a single reaction, we generated one site (thrill) that was not detected with any of the four kinases alone, this residue is not phosphorylated by any other known kinase in vitro. Phosphorylation at this residue is also present in PHF-tau. These results show that combinations of kinases can result in phosphorylation at new sites, possibly due to conformational changes induced by the primary phosphorylation step that increase the likelihood of the secondary phosphorylat ion, possibly by a second enzyme.

Amyloid Beta Treatment of Neurons

We found that treatment of neurons with Aβ peptide increased tyrosine phosphorylation of neuronal proteins including tau. The increase in phosphotyrosine induced by Aβ was approximately four times the basal level in tau.

Future Experiments

Identify phosphorylation sites of other individual and combinations of protein kinases to emulate PHF-tau phosphorylation in vitro. Kinases that have been implicated in tauopathies include GSK=3α, ERKs 1 & 2, cdk5, cdc2 kinase, JNK, several members of the SAP kinase family (1γ, 2a, 2b, 3, 4), p38MAP kinase, calmodulin-dependent kinase, PKC, MARK, PKN, PKB, TTK, DYRK, Rho kinase and phosphorylase kinase.

Determine if phosphorylation of tau with these kinases and other tyrosine kinases induces tau aggregation in vitro and in cells. This will allow us to identify the phosphorylation sites that are critical for tau aggregation.

Investigate the effects of specific protein kinase inhibitors, alone and in combination, on tau aggregation in an in vitro or cellular context.

Generate transgenic mice (inducibly) expressing CK1 and determine if this model shows cerebral tau deposition. Cross this mouse with other mice expressing candidate kinases (eg a GSK-3 mouse already exists) and examine the rate of tangle formation.

We have recently found (unpublished) that tyr394 is phosphorylated in AD and in foetal tau and have reported that this same residue is phosphorylated by both Fyn and Lck in vitro. Fyn has been shown previously to phosphorylate tau and Fyn is increased in a sub-set of neurons in AD. It is also known that Aβ treatment of neurons induces tau phosphorylation and that Fyn knock-out mice are resistant to Aβ.

We will treat neurons from wild-type, Fyn knock-out and Src knock-out mice with Aβ and identify the phosphorylation sites on tau in each case.

It is possible that other tyrosine kinases are involved in tau phosphorylation and aggregation and these include those associated with growth factor and neurotrophic factor receptors. Other tyrosine kinase families may also be involved, including Syk kinase, which has been show to phosphorylate another protein (α-synuclein) implicated in neurodegenerative disease in a manner that increases its propensity to aggregate in vitro. In each case, we will investigate the effects of phosphorylation on tau aggregation and the effects of kinase inhibition on tau aggregation.

TABLE 1

New sites identified in tau as phosphorylated by individual serine/threonine kinases

| Kinase | New sites identified in recombinant tau | New sites present in PHF-tau | Kinase sites present in 12 new PHF-tau sites |
|---|---|---|---|
| CK1 | (46/50), 113, 131, 149, 169, 184, 208, (210, 212), 214, 237, 238, 241, 258, 262, 263, 285, 289, 305, 341, 352, 356, 361, 373, 386, (412/413/414/416, 2 sites), 416, 433, 435 | 113, 184, 208, (210, 212), 214, 237, 238, 258, 262, 289, 356, (412/413/414/416, 2 sites), 416, 433, 435 | (111/113), 258, 289, 416, 433, 435 (412/413/414/416, 2 sites) |

TABLE 1-continued

New sites identified in tau as phosphorylated by individual serine/threonine kinases

| Kinase | New sites identified in recombinant tau | New sites present in PHF-tau | Kinase sites present in 12 new PHF-tau sites |
|---|---|---|---|
| CK2 | (52/56), 199, 386, 400, (412/413/414/416, 1 site) | 199, 400, (412/413/414/416, 1 site) | (412/413/414/416, 1 site) |
| GSK-3 | 149, 220, 237, 241, 245, 258, 285, 289, 305, 352, 373, (409/412/413/414/416, 2 sites of which 1 or 2 are new) | 237, 258, 289, (409/412/413/414/416, 2 sites of which 1 or 2 are new) | 258, 289, (409/412/413/414/416, 2 sites of which 1 or 2 are new) 69 (this site is already known for GSK, but is new in PHF-tau) |
| PKA | 210, (217/220), 258, 352, (412/413) | 210, (217/220), 258, (412/413) | 258, 416 |

The 12 new sites in PHF-tau are:
68, 69, 71, (111/113), 191, 258, 289, Y394, (414/416), 427, 433, 435

TABLE 2

| Site | PHF-tau | Kinase Mix | CK1 | CK2 | GSK-3β | PKA | Site |
|---|---|---|---|---|---|---|---|
| T17 | | | | | | | T17 |
| Y18 | A | | | | | | Y18 |
| Y29 | | | | | | | Y29 |
| T30 | | | | | | | T30 |
| T39 | | | | * | | | T39 |
| S46 | A | | ½N | | * | | S46 |
| T50 | | | ½N | | * | | T50 |
| T52 | | | | ½N | | | T52 |
| S56 | | | | ½N | | | S56 |
| S61 | | | | | | | S61 |
| S64 | | | | | | | S64 |
| S68 | * | | | | | | S68 |
| T69 | * | | | | * | | T69 |
| T71 | * | | | | | | T71 |
| T76 | | | | | | | T76 |
| T95 | | | | | | | T95 |
| T101 | | | | | | | T101 |
| T102 | | | | | | | T102 |
| T111 | ½ | * | | | | | T111 |
| S113 | ½ | * | | *N | | | S113 |
| T123 | ? | | | | | | T123 |
| S129 | | | | | | | S129 |
| S131 | | | *N | | | | S131 |
| T135 | | | | | | | T135 |
| S137 | ? | | | | | | S137 |
| T149 | | * | *N | | *N | | T149 |
| T153 | A? | | | | * | | T153 |
| T169 | | | *N | | | | T169 |
| T175 | * | * | | | * | | T175 |

TABLE 2-continued

| Site | PHF-tau | Kinase Mix | CK1 | CK2 | GSK-3β | PKA | Site |
|---|---|---|---|---|---|---|---|
| T181 | * | * | | | * | * | T181 |
| S184 | ½ | | *N | | * | * | S184 |
| S185 | ½ | | | | | | S185 |
| S191 | * | | | | | | S191 |
| S195 | | | | | | * | S195 |
| Y197 | | | | | | | Y197 |
| S198 | * | | | | * | * | S198 |
| S199 | * | | | *N | * | * | S199 |
| S202 | * | | | | * | * | S202 |
| T205 | A | | | | * | * | T205 |
| S208 | * | | *N | | (*) | | S208 |
| S210 | * | *½ | ½N | | ½ | *N | S210 |
| T212 | * | ½ | ½N | | *½ | * | T212 |
| S214 | * | * | *N | | * | * | S214 |
| T217 | * | * | | | * | ½N | T217 |
| T220 | ? | | | *N | ½N | | T220 |
| T231 | * | * | | | * | * | T231 |
| S235 | * | 2/3 | | | * | * | S235 |
| S237 | * | 2/3 | *N | | *N | | S237 |
| S238 | * | 2/3 | *N | | | | S238 |
| S241 | | | *N | | *N | | S241 |
| T245 | | | | | *N | * | T245 |
| S258 | * | * | *N | | *N | *N | S258 |
| S262 | * | * | *N | | * | * | S262 |
| T263 | * | *N | | | | | T263 |
| S285 | | | *N | *N | | | S285 |
| S289 | * | * | *N | | *N | | S289 |
| S293 | | | | | | * | S293 |
| S305 | | * | *N | | *N | * | S305 |
| Y310 | | | | | | | Y310 |
| S316 | | | | | | | S316 |
| S319 | | | | | | | S319 |
| S320 | | | | | | * | S320 |
| S324 | * | | | | * | * | S324 |
| S341 | | | *N | | | | S341 |
| S352 | | * | *N | | *N | *N | S352 |
| S356 | * | * | *N | | * | * | S356 |
| T361 | | * | *N | | | | T361 |
| T373 | * | * | *N | | *N | *N | T373 |
| T377 | | | | | | | T377 |
| T386 | | | *N | *N | | | T386 |
| Y394 | * | | | | | | Y394 |
| S396 | * | * | * | * | * | * | S396 |
| S400 | * | * | | *N | * | * | S400 |
| T403 | * | ½ | | | (*) | (*) | T403 |
| S404 | * | ½ | * | * | * | * | S404 |
| S409 | * | * | | | 2/5N | * 3/5 | S409 |
| S412 | * | 2/4 | 2/4N | ¼N | 2/5N | ½N 3/5 | S412 |
| S413 | * | 2/4 | 2/4N | ¼N | *2/5N | ½N 3/5 | S413 |
| T414 | ½ | 2/4 | 2/4N | ¼N | 2/5N | 3/5 | T414 |
| S416 | ½ | *2/4 | *2/4N | ¼N | 2/5N | * 3/5 | S416 |
| S422 | * | | | | | * | S422 |
| T427 | * | | | | | | T427 |
| S433 | * | ½ | *N | | | | S433 |
| S435 | * | ½ | *N | | | | S435 |
| Site | PHF-tau | Kinase Mix | CK1 | CK2 | GSK-3β | PKA | Site |

* = identified phosphorylation site

A = identified by antibody labelling; ½ etc = one of two adjacent sites phosphorylated in PHF-tau; ? = suspected sites in PHF-tau New PHF-tau sites indicated in red.

Kinase phosphorylation sites

Shaded sited indicate multiple (numbered) phosphorylations at less well-defined sites, N indicates a new site.

Some of the kinase phosphorylation sites were identified using antibodies

Kinase sites identified by MS or antibodies are all compiled together in this table (*) = GSK is phosphorylated on these sites after priming at other sites

TABLE 3

| Site | PHF-tau | No known kinase | CK1 GSK-3 PKA | Mix of 4 kinases | CK1 | CK2 | GSK-3β | PKA | Control tau | PHF-tau | Site |
|---|---|---|---|---|---|---|---|---|---|---|---|
| S68 | * | * | | | | | | | | * | S68 |
| T69 | * | | * | | | | * | | | * | T69 |
| T71 | * | * | | | | | | | | * | T71 |
| T111 | ½ | | | * | | | | | | ½ | T111 |
| S113 | ½ | | * | * | *N | | | | | ½ | S113 |
| T175 | * | | * | * | | | * | | | * | T175 |
| T181 | * | | * | * | | | * | | * | * | T181 |
| S184 | ½ | | * | | *N | | * | | | ½ | S184 |
| S185 | ½ | | | | | | | | | ½ | S185 |
| S191 | * | * | | | | | | | | * | S191 |
| S198 | * | | * | | | | * | * | * | * | S198 |
| S199 | * | | * | | | *N | * | * | * | * | S199 |
| S202 | * | | * | | | | * | * | * | * | S202 |
| S208 | * | | * | | *N | | (*) | | | * | S208 |
| S210 | * | | * | * ½ | ½N | | ½ | *N | | * | S210 |
| T212 | * | | * | | ½ | ½N | *½ | * | * | * | T212 |
| S214 | * | | * | * | *N | | * | * | | * | S214 |
| T217 | * | | * | * | | | * | ½N | * | * | T217 |
| T231 | * | | * | * | | | * | * | * | * | T231 |
| S235 | * | | * | 2/3 | | | * | * | * | * | S235 |
| S237 | * | | * | 2/3 | *N | | *N | | | * | S237 |
| S238 | * | | * | 2/3 | *N | | | | | * | S238 |
| S258 | * | | * | * | *N | | *N | *N | | * | S258 |
| S262 | * | | * | * | *N | | * | * | | * | S262 |
| S289 | * | | * | * | *N | | *N | | | * | S289 |
| S356 | * | | * | * | *N | | * | * | | * | S356 |
| Y394 | ? | * | | | | | | | | ? | Y394 |
| S396 | * | | * | * | * | * | * | | * | * | S396 |
| S400 | * | | * | * | | *N | * | | * | * | S400 |
| T403 | * | | * | ½ | | | (*) | | | * | T403 |
| S404 | * | | * | ½ | * | * | * | | * | * | S404 |
| S409 | * | | * | * | | | 2/5N | * 3/5 | | * | S409 |
| S412 | * | * | (*) | 2/4 | 2/4N | 1/4N | 2/5N | ½N 3/5 | 3/4 | * | S412 |
| S413 | * | | | 2/4 | 2/4N | 1/4N | *2/5N | ½N 3/5 | 3/4 | * | S413 |
| T414 | ½ | * | (*) | 2/4 | 2/4N | 1/4N | 2/5N | 3/5 | 3/4 | ½ | T414 |
| S416 | ½ | | * | *2/4 | *2/4N | 1/4N | 2/5N | * 3/5 | * 3/4 | ½ | S416 |
| S422 | * | | * | | | | | * | | * | S422 |
| T427 | * | * | | | | | | | | * | T427 |
| S433 | * | | * | ½ | *N | | | | | * | S433 |
| S435 | * | | * | ½ | *N | | | | | * | S435 |
| Site | PHF-tau | No known kinase | CK1 GSK-3 PKA | Mix of 4 kinases | CK1 | CK2 | GSK-3β | PKA | Control tau | PHF-tau | Site |

REFERENCES

The references mentioned herein are all expressly incorporated by reference.

Ghoshal N, Smiley J F, DeMaggio A J, Hoekstra M F, Cochran E J, Binder L I, Kuret J. (1999) A new molecular link between the fibrillar and granulovacuolar lesions of Alzheimer's disease. Am J. Pathol. 155, 1163-72.

Hanger D P, Betts J C, Loviny T L, Blackstock W P, Anderton B H. (1998) New phosphorylation sites identified in hyperphosphorylated tau (paired helical filament-tau) from Alzheimer's disease brain using nanoelectrospray mass spectrometry. J. Neurochem. 71, 2465-76.

Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A., and Klein, W. L. (1998). Diffusible, non-fibrillar ligands derived from $A\beta_{1-42}$ are potent central nervous system neurotoxins. Proc. Natl. Acad. Sci. USA 95, 6448-6453.

Lee V M, Goedert M, Trojanowski J Q. (2001) Neurodegenerative tauopathies. Annu Rev Neurosci. 24, 1121-59.

Mulot S F, Hughes K, Woodgett J R, Anderton B H, Hanger D P. (1994) PHF-tau from Alzheimer's brain comprises four species on SDS-PAGE which can be mimicked by in vitro phosphorylation of human brain tau by glycogen synthase kinase-3 beta. FEBS Lett. 349, 359-64.

Scales, T M E, Williamson, R., Anderton, B H, Renolds, C H et al (2002) Tyrosine phosphorylation of specific sites on tau by Src family kinases. Neurobiol Aging 23, S500-501.

Shirazi, S. K. and Wood, J. G. (1993). The protein tyrosine kinase, fyn, in Alzheimer's disease pathology. Neuroreport 4, 435-437.

Singh T J, Zaidi T, Grundke-Iqbal I, Iqbal K. (1995a) Modulation of GSK-3-catalyzed phosphorylation of microtubule-associated protein tau by non-proline-dependent protein kinases. FEBS Lett. 358, 4-8.

Singh T J, Hague N, Grundke-Iqbal I, Iqbal K. (1995b) Rapid Alzheimer-like phosphorylation of tau by the synergistic actions of non-proline-dependent protein kinases and GSK-3. FEBS Lett. 358, 267-72.

Williamson, R., Scales, T., Clark, B. R., Gibb, G., Reynolds, C. H., Kellie, S., Bird, I. N., Varndell, I. M., Sheppard, P. W., Everall, I., and Anderton, B. H. (2002). Rapid tyrosine phosphorylation of neuronal proteins including tau and focal adhesion kinase in response to amyloid-β peptide exposure: involvement of Src family protein kinases. J. Neurosci. 22, 10-20.

The invention claimed is:

1. A method of screening for a candidate substance which inhibits the phosphorylation of a tau protein at sites phosphorylated by casein kinase 1 (CK1), the method consisting of:
   (a) contacting under reaction conditions suitable to effect phosphorylation of said sites by CK1,
      i) said candidate substance;
      ii) a tau protein comprising the amino acid sequence of SEQ ID NO:2, or a tau variant comprising an amino acid sequence that is at least 95% identical to the amino acid sequence of SEQ ID NO:2, said tau protein or tau variant including one or more phosphorylation sites S46, T50, S113, S131, T149, T169, S184, S208, S210, T212, S214, S237, S238, S241, S258, S262, T263, S285, S289, S305, S341, S352, S356, T361, T373, T386, S412, S413, T414, S416, S433 and S435, said phosphorylation sites corresponding to the amino acid sequence of SEQ ID NO:2; and each of said sites being a substrate for CK1 kinase,
      iii) a CK1 polypeptide comprising the amino acid sequence of SEQ ID NO: 1, or a CK1 variant comprising an amino acid sequence that is at least 95% identical to the amino acid sequence of SEQ ID NO:1, wherein said CK1 polypeptide or CK1 variant phosphorylates the tau protein or the tau variant of ii) at one or more sites selected from the group consisting of (S46/T50), S113, S131, T149, T169, S184, S208, (S210/T212), S214, S237, S238, S241, S258, S262, T263, S285, S289, S305, S341, S352, S356, T361, T373, T386, (S412/S413/T414), S416, S433 and S435 corresponding to the amino acid sequence of SEQ ID NO:2;
   (b) determining whether, and optionally the extent to which the candidate substance of i) inhibits phosphorylation of the tau protein or tau variant of ii) by the CK1 polypeptide or CK1 variant of iii) at one or more sites selected from the group consisting of (S46/T50), S113, S131, T149, T169, S184, S208, (S210/T212), S214, S237, S238, S241, S258, S262, T263, S285, S289, S305, S341, S352, S356, T361, T373, T386, (S412/S413/T414), S416, S433 or S435 corresponding to the amino acid sequence of SEQ ID NO:2; and (c) selecting the candidate substance that inhibits CK1-mediated phosphorylation of said tau protein or tau variant at one or more phosphorylation sites.

2. The method of claim 1, wherein the tau protein of ii) is paired helical filament tau (PHF-tau).

3. The method of claim 1, wherein the tau protein of ii) is a fragment of SEQ ID NO: 2 having one or more of said phosphorylation sites.

4. The method of claim 1, wherein the sites of the tau protein are selected from S262 and/or S356 corresponding to the amino acid sequence of SEQ ID NO:2.

5. The method of claim 1, wherein the sites of the tau protein are one or more sites selected from the group consisting of S113, S258, S289, S416, S433 and S435 corresponding to the amino acid sequence of SEQ ID NO:2.

6. A method of screening for a candidate substance which inhibits the phosphorylation of a tau protein at sites phosphorylated by casein kinase 1 (CK1), the method consisting of:
   (a) contacting, under reaction conditions suitable to effect phosphorylation of said sites by CK1,
   i) said candidate substance;
   ii) a tau protein comprising the amino acid sequence of SEQ ID NO:2, or a tau variant comprising an amino acid sequence that is at least 95% identical to the amino acid sequence of SEQ ID NO:2, said tau protein or tau variant including one or more phosphorylation sites S46, T50, S113, S131, T149, T169, S184, S208, S210, T212, S214, S237, S238, S241, S258, S262, T263, S285, S289, S305, S341, S352, S356, T361, T373, T386, S412, S413, T414, S416, S433 and S435, said phosphorylation sites corresponding to the amino acid sequence of SEQ ID NO:2 and each being a phosphorylation site for CK1 kinase;
   iii) a CK1 polypeptide comprising the amino acid sequence of SEQ ID NO: 1, or a CK1 variant comprising an amino acid sequence that is at least 95% identical to the amino acid sequence of SEQ ID NO:1, wherein said CK1 polypeptide or CK1 variant phosphorylates the tau protein or the tau variant of ii) at one or more sites selected from the group consisting of (S46/T50), S113, S131, T149, T169, S184, S208, (S210/T212), S214, S237, S238, S241, S258, S262, T263, S285, S289, S305, S341, S352, S356, T361, T373, T386, (S412/S413/T414), S416, S433 and S435 corresponding to the amino acid sequence of SEQ ID NO:2;

(b) determining whether, and optionally the extent to which the candidate substance of i) inhibits phosphorylation of the tau protein or tau variant of ii) by the CK1 polypeptide or CK1 variant of iii) at one or more sites selected from the group consisting of (S46/T50), S113, S131, T149, T169, S184, S208, (S210/T212), S214, S237, S238, S241, S258, S262, T263, S285, S289, S305, S341, S352, S356, T361, T373, T386, (S412/S413/T414), S416, S433 or S435 corresponding to the amino acid sequence of SEQ ID NO:2;

(c) selecting the candidate substance that inhibits CK1-mediated phosphorylation of said tau protein or tau variant at one or more phosphorylation sites, and (d) as follows: (d) determining whether, and optionally the extent to which, the candidate substance inhibits the phosphorylation of another substrate by the casein kinase 1.

7. The method of claim 6, wherein step (d) confirms whether the selected candidate substance in (c) inhibits the phosphorylation of the tau protein.

8. The method of claim 1, wherein the step of determining whether and optionally the extent of phosphorylation at the one or more sites of the tau protein employs mass spectroscopy or a site specific recognition agent which is capable of distinguishing between a phosphorylated and a non-phosphorylated site.

9. The method of claim 1, wherein the screening is carried out in a multiplex assay employing a solid phase on which a plurality of the tau proteins are immobilised.

10. The method of claim 9, wherein the tau proteins are PHF-tau proteins.

11. The method of claim 1, said phosphorylation site(s) being at least one selected from the group consisting of S113, S237, S238, S258, S289, S412, S413, T414, S416, S433, and S435 corresponding to the amino acid sequence of SEQ ID NO: 2; and said sites having been previously identified as phosphorylated in clinical PHF-tau by casein kinase 1.

* * * * *

SEQUENCE LISTING

<160> NUMBER OF SEQ ID NOS: 3

<210> SEQ ID NO 1
<211> LENGTH: 428
<212> TYPE: PRT
<213> ORGANISM: Rattus norvegicus

<400> SEQUENCE: 1

```
Met Glu Leu Arg Val Gly Asn Arg Tyr Arg Leu Gly Arg Lys Ile Gly
1               5                   10                  15

Ser Gly Ser Phe Gly Asp Ile Tyr Leu Gly Thr Asp Ile Ala Ala Gly
            20                  25                  30

Glu Glu Val Ala Ile Lys Leu Glu Cys Val Lys Thr Lys His Pro Gln
        35                  40                  45

Leu His Ile Glu Ser Lys Ile Tyr Lys Met Met Gln Gly Gly Val Gly
    50                  55                  60

Ile Pro Thr Ile Arg Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
    210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ala Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
        275                 280                 285

Asp Trp Asn Met Leu Lys Phe Gly Ala Ser Arg Ala Ala Asp Asp Ala
    290                 295                 300

Glu Arg Glu Arg Arg Asp Arg Glu Arg Leu Arg His Ser Arg Asn
305                 310                 315                 320

Pro Ala Thr Arg Gly Leu Pro Ser Thr Ala Ser Gly Arg Leu Arg Gly
                325                 330                 335

Thr Gln Glu Val Ala Pro Pro Thr Pro Leu Thr Pro Thr Ser His Thr
            340                 345                 350

Ala Asn Thr Ser Pro Arg Pro Val Ser Gly Met Glu Arg Glu Arg Lys
        355                 360                 365
```

```
Val Ser Met Arg Leu His Arg Gly Ala Pro Val Asn Val Ser Ser Ser
            370                 375                 380

Asp Leu Thr Gly Arg Gln Asp Thr Ser Arg Met Ser Thr Ser Gln Arg
385                 390                 395                 400

Ser Arg Asp Met Ala Ser Leu Arg Leu His Ala Ala Arg Gln Gly Ala
                405                 410                 415

Arg Cys Arg Pro Gln Arg Pro Arg Arg Thr Thr Tyr
            420                 425

<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320
```

```
Lys Cys Gly Ser Leu Gly Asn Ile His His Lys Pro Gly Gly Gly Gln
            325                 330             335

Val Glu Val Lys Ser Glu Lys Leu Asp Phe Lys Asp Arg Val Gln Ser
            340                 345             350

Lys Ile Gly Ser Leu Asp Asn Ile Thr His Val Pro Gly Gly Gly Asn
            355                 360             365

Lys Lys Ile Glu Thr His Lys Leu Thr Phe Arg Glu Asn Ala Lys Ala
            370                 375             380

Lys Thr Asp His Gly Ala Glu Ile Val Tyr Lys Ser Pro Val Val Ser
385                 390                 395             400

Gly Asp Thr Ser Pro Arg His Leu Ser Asn Val Ser Ser Thr Gly Ser
            405                 410             415

Ile Asp Met Val Asp Ser Pro Gln Leu Ala Thr Leu Ala Asp Glu Val
            420                 425             430

Ser Ala Ser Leu Ala Lys Gln Gly Leu
            435                 440

<210> SEQ ID NO 3
<211> LENGTH: 537
<212> TYPE: PRT
<213> ORGANISM: Homo sapiens

<400> SEQUENCE: 3

Met Gly Cys Val Gln Cys Lys Asp Lys Glu Ala Thr Lys Leu Thr Glu
1               5                   10                  15

Glu Arg Asp Gly Ser Leu Asn Gln Ser Ser Gly Tyr Arg Tyr Gly Thr
            20                  25                  30

Asp Pro Thr Pro Gln His Tyr Pro Ser Phe Gly Val Thr Ser Ile Pro
        35                  40                  45

Asn Tyr Asn Asn Phe His Ala Ala Gly Gly Gln Gly Leu Thr Val Phe
    50                  55                  60

Gly Gly Val Asn Ser Ser Ser His Thr Gly Thr Leu Arg Thr Arg Gly
65                  70                  75                  80

Gly Thr Gly Val Thr Leu Phe Val Ala Leu Tyr Asp Tyr Glu Ala Arg
                85                  90                  95

Thr Glu Asp Asp Leu Ser Phe His Lys Gly Glu Lys Phe Gln Ile Leu
            100                 105                 110

Asn Ser Ser Glu Gly Asp Trp Trp Glu Ala Arg Ser Leu Thr Thr Gly
        115                 120                 125

Glu Thr Gly Tyr Ile Pro Ser Asn Tyr Val Ala Pro Val Asp Ser Ile
    130                 135                 140

Gln Ala Glu Glu Trp Tyr Phe Gly Lys Leu Gly Arg Lys Asp Ala Glu
145                 150                 155                 160

Arg Gln Leu Leu Ser Phe Gly Asn Pro Arg Gly Thr Phe Leu Ile Arg
                165                 170                 175

Glu Ser Glu Thr Thr Lys Gly Ala Tyr Ser Leu Ser Ile Arg Asp Trp
            180                 185                 190

Asp Asp Met Lys Gly Asp His Val Lys His Tyr Lys Ile Arg Lys Leu
        195                 200                 205

Asp Asn Gly Gly Tyr Tyr Ile Thr Thr Arg Ala Gln Phe Glu Thr Leu
    210                 215                 220

Gln Gln Leu Val Gln His Tyr Ser Glu Arg Ala Ala Gly Leu Cys Cys
225                 230                 235                 240

Arg Leu Val Val Pro Cys His Lys Gly Met Pro Arg Leu Thr Asp Leu
```

-continued

```
                245                 250                 255
Ser Val Lys Thr Lys Asp Val Trp Glu Ile Pro Arg Glu Ser Leu Gln
            260                 265                 270

Leu Ile Lys Arg Leu Gly Asn Gly Gln Phe Gly Glu Val Trp Met Gly
            275                 280                 285

Thr Trp Asn Gly Asn Thr Lys Val Ala Ile Lys Thr Leu Lys Pro Gly
            290                 295                 300

Thr Met Ser Pro Glu Ser Phe Leu Glu Glu Ala Gln Ile Met Lys Lys
305                 310                 315                 320

Leu Lys His Asp Lys Leu Val Gln Leu Tyr Ala Val Val Ser Glu Glu
            325                 330                 335

Pro Ile Tyr Ile Val Thr Glu Tyr Met Asn Lys Gly Ser Leu Leu Asp
            340                 345                 350

Phe Leu Lys Asp Gly Glu Gly Arg Ala Leu Lys Leu Pro Asn Leu Val
            355                 360                 365

Asp Met Ala Ala Gln Val Ala Ala Gly Met Ala Tyr Ile Glu Arg Met
            370                 375                 380

Asn Tyr Ile His Arg Asp Leu Arg Ser Ala Asn Ile Leu Val Gly Asn
385                 390                 395                 400

Gly Leu Ile Cys Lys Ile Ala Asp Phe Gly Leu Ala Arg Leu Ile Glu
            405                 410                 415

Asp Asn Glu Tyr Thr Ala Arg Gln Gly Ala Lys Phe Pro Ile Lys Trp
            420                 425                 430

Thr Ala Pro Glu Ala Ala Leu Tyr Gly Arg Phe Thr Ile Lys Ser Asp
            435                 440                 445

Val Trp Ser Phe Gly Ile Leu Leu Thr Glu Leu Val Thr Lys Gly Arg
            450                 455                 460

Val Pro Tyr Pro Gly Met Asn Asn Arg Glu Val Leu Glu Gln Val Glu
465                 470                 475                 480

Arg Gly Tyr Arg Met Pro Cys Pro Gln Asp Cys Pro Ile Ser Leu His
            485                 490                 495

Glu Leu Met Ile His Cys Trp Lys Lys Asp Pro Glu Glu Arg Pro Thr
            500                 505                 510

Phe Glu Tyr Leu Gln Ser Phe Leu Glu Asp Tyr Phe Thr Ala Thr Glu
            515                 520                 525

Pro Gln Tyr Gln Pro Gly Glu Asn Leu
530                 535
```